Figure 1:
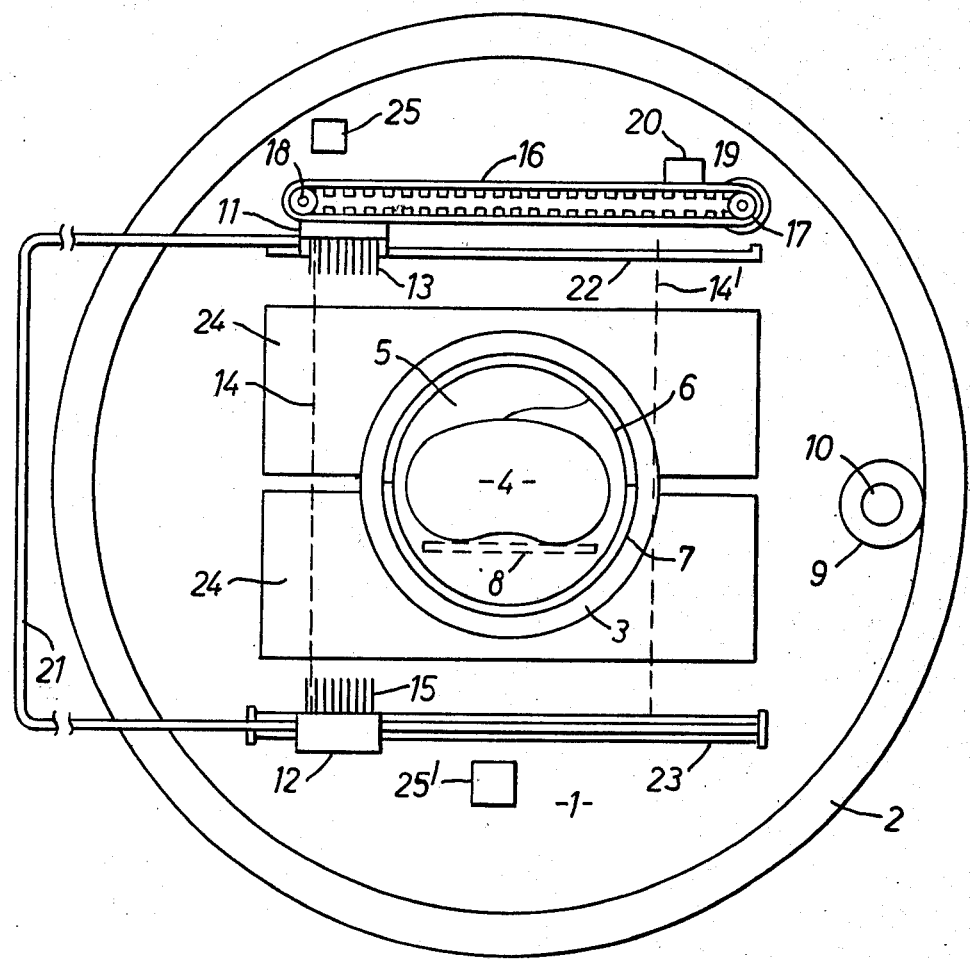

United States Patent [19]

Froggatt et al.

[11] 3,996,467

[45] Dec. 7, 1976

[54] DATA ACQUISITION IN TOMOGRAPHY

[75] Inventors: Robert Justin Froggatt, Southall; William Spencer Percival, London, both of England

[73] Assignee: EMI Limited, Hayes, England

[22] Filed: May 15, 1975

[21] Appl. No.: 577,625

[30] Foreign Application Priority Data

May 15, 1974 United Kingdom ............ 21528/74

[52] U.S. Cl. .............................. 250/366; 250/368; 250/445 T

[51] Int. Cl.² ........................................ G03B 41/16

[58] Field of Search .......... 250/320, 321, 322, 323, 250/358, 359, 360, 363, 366, 368, 369, 445 T

[56] References Cited

UNITED STATES PATENTS 3,778,614    12/1973    Hounsfield ..................... 250/445 T

*Primary Examiner*—Craig E. Church
*Attorney, Agent, or Firm*—Fleit & Jacobson

[57] ABSTRACT

In an apparatus for examining a body with penetrating radiation a source and detector arrangement scan about the body to irradiate the body along a plurality of beam paths lying in a plane. Output signals are provided from weighted components where each component relates to the absorption of the radiation along one of a set of adjacent and substantially parallel beam paths. The weighting is according to a function chosen so that the output signals are restricted to a chosen spatial frequency band to reduce errors in a representation, if the distribution of absorption of the radiation through the body, constructed from the output signals. The weighting may be provided by optical means between scintillator crystals and photomultipliers forming the detector arrangement.

9 Claims, 6 Drawing Figures

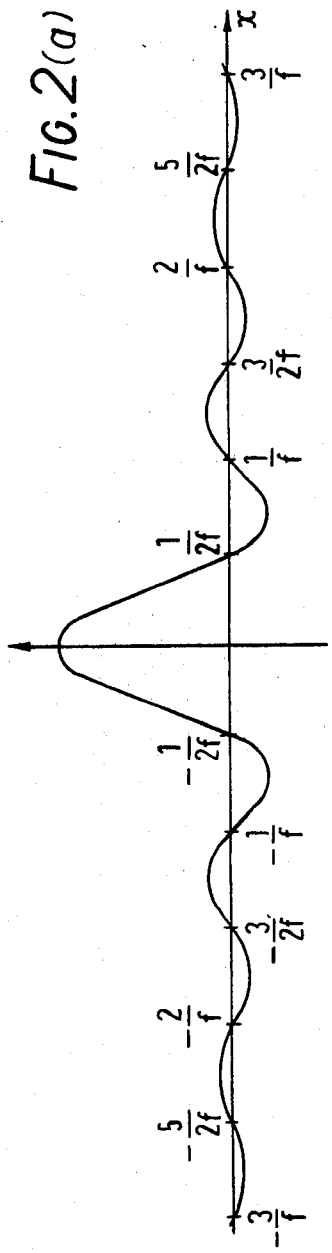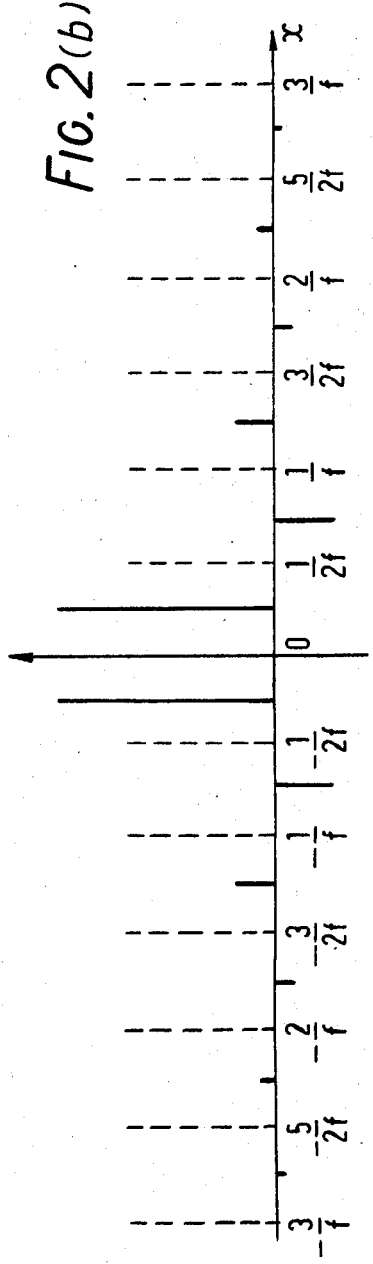
FIG.2(a)
FIG.2(b)

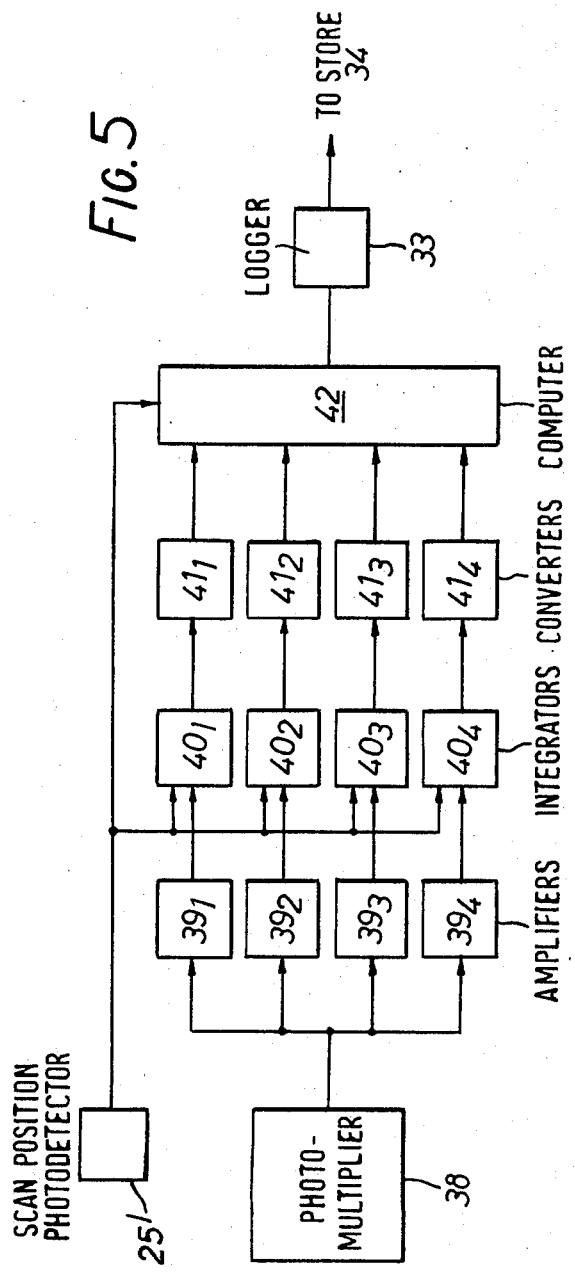

DATA ACQUISITION IN TOMOGRAPHY

This invention relates to apparatus for examining a body by means of radiation such as X- or γ- radiation.

In the specification of U.S. Pat. No. 3,778,614 there is described apparatus, for carrying out such examinations, in which a source of radiation and detecting means are mounted to face each other across an aperture in which the body to be examined can be located, the apparatus being intended primarily for examination of part of the human body. The detecting means is arranged to detect a narrow beam of radiation transmitted from the source through the body. Locating means are provided for locating the part of the body to be examined in the aperture and the latter may be adapted to receive, for example, the head or some other part of the human body. In order to carry out the examination, scanning means are provided for producing inter-related orbital and lateral scanning movements of the source and the detecting means in a plane normal to the axis of the aperture so that the beam of radiation to which the detecting means is sensitive scans the body to be examined in a direction substantially normal to its length, due to the lateral scanning movements, and with many different orientations resulting from the orbital scanning movement. During each lateral scan a set of output signals is derived from the detecting means representing the transmission or the absorption of the body, with respect to the radiation, along a set of closely spaced, substantially parallel, beam paths in the said plane.

Since a lateral scan occurs for each of a series of successive increments of the orbital scanning movement successive sets of signals are derived corresponding to sets of closely spaced paths orientated at different angles or mean angles. From the many sets of output signals, a representation of a variable transmission or absorption in the planar section of the body under examination can be produced.

Each set of output signals constitutes a sampling of this basic data, an image of which is to be produced, and, as the sampling is in fact performed, according to a sensibly uniform sampling sequence.

It is known that a sampled function which at all points is finite and continuous can in principle be reconstructed free of error from a large number of samples of the function taken at uniform intervals, if these intervals are sufficiently small, that is to say if the sampling occurs at a sufficiently high rate. This rate must be at least twice the repetition frequency of the highest order Fourier component of the sampled function, otherwise the function cannot be regained without error.

A difficulty present in the construction of such apparatus is that in some circumstances, such as can arise in the examination of a human body for the purposes of medical diagnosis, an object present in the field of examination, for example a bone structure, can present spatial rates of change calling for impracticably or undesirably high rates of sampling to meet the sampling requirement stated. If the requirement is not met then reconstruction of the absorption pattern from the sampled data tends to spread the resulting errors and so give rise to superposed spurious patterns.

The difficulty can be mitigated by appropriately increasing the collimation aperture of the exploring beam so that the examined data becomes effectively band limited to the half sampling rate frequency by virtue of the process of acquisition of the data. This procedure is not entirely satisfactory, since it tends to cause appreciable attenuation of the higher Fourier components of the data in the acquisition band. If, as can be done with suitable convolution processing of the data to reconstruct the absorption pattern, such components are emphasised in the reconstruction so as to restore to some extent at least the corresponding loss of resolution in the image, then statistical noise in the emphasis band of frequencies is increased.

An object of the invention is to avoid or substantially avoid, such loss of performance in regard to noise.

According to the invention there is provided an apparatus for examining a body by means of penetrating radiation such as X- or γ- radiation including source means arranged to irradiate a substantially planar region of the body, detector means responsive to said radiation and disposed to receive the radiation after passage through the body, means for scanning the source and detector means about the body to irradiate the body along a plurality of beam paths in the plane of said region wherein the apparatus is arranged to provide output signals constructed from weighted components, each component related to the intensity of radiation received along one of a set of adjacent and substantially parallel ones of said beam paths, the weighting being according to a predetermined function so that said output signals are limited to a predetermined spatial frequency band and further including means arranged to provide signals, which are logarithms of said output signals, for processing to construct a representation of the distribution of absorption with position in the said planar region.

Figure 3:
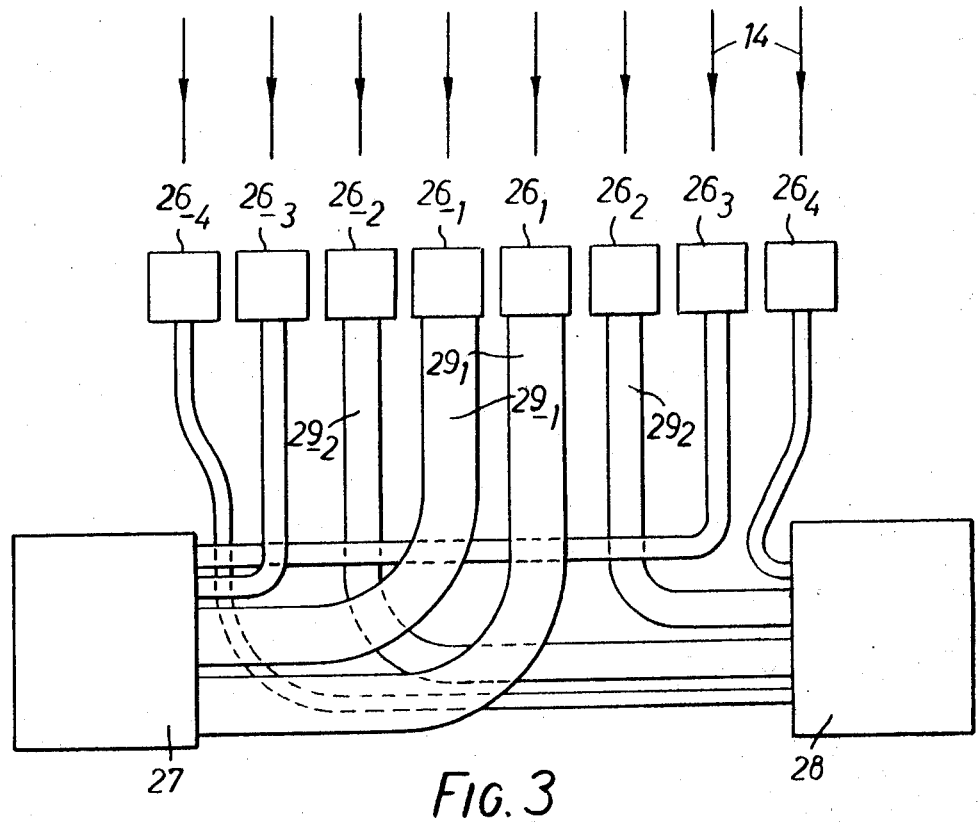
Figure 4:
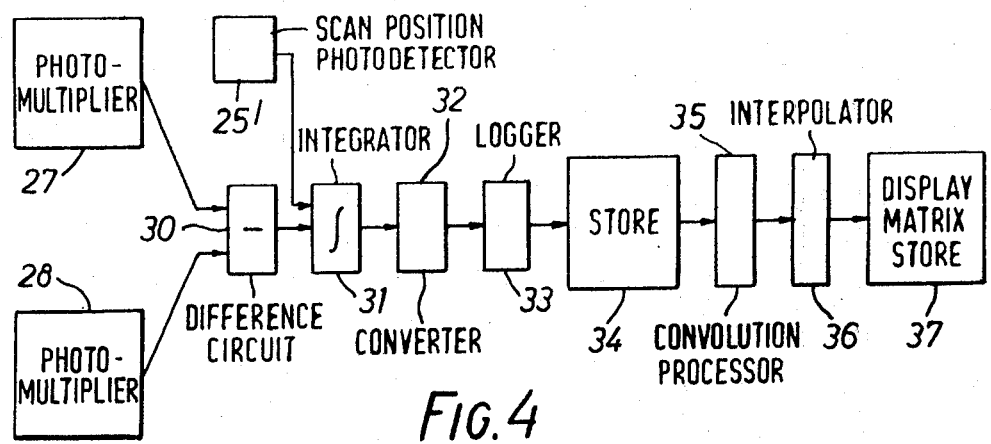

In order that the invention may be clearly understood and readily carried into effect it will now be described by way of example with reference to the accompanying drawings in which:

FIG. 1 illustrates a form of scanning equipment in accordance with the invention;

FIGS. 2(a) and 2(b) are diagrams relating to a form of weighting in accordance with the invention;

FIG. 3 shows apparatus for achieving the weighting;

FIG. 4 sets out the general nature of means suitable for converting data samples acquired by means of the arrangement of FIG. 2 into data suitable for displaying as a reconstruction of the absorption pattern examined; and FIG. 5 shows an alternative processing arrangement suitable for use with a further embodiment of the invention.

Referring to the drawings, FIG. 1 shows a form of the apparatus for the purpose referred to hereinbefore. The apparatus comprises a rotary member 1 which is rotatable inside a fixed casing 2 forming part of the main frame of the apparatus. The rotary member has a central aperture 3 in which the part of the patients body to be examined can be inserted. In the region of the exploring radiation the patients body 4 is surrounded by a suitable medium, which in this case is water, having an absorption coefficient for the radiation closely similar to that of body tissue. The water is shown in the figure at 5 and is contained within an envelope or bag 6. The envelope is positioned within a ring-like structure 7 which may be of metal such as duralumin.

The ring member 7 is in two parts as described in U.S.A. application Ser. No. 476,300 and may be, for example, fixed to a supporting means 8 arranged to support the patient. Ring 7 does not share in the rotary motion which, as will be described, is imparted to the surrounding apparatus.

A toothed gear wheel 9, driven by a motor 10, is provided for driving the rotatable member 1 so as to produce orbital motion of the member about its axis, which is also the axis of the aperture 3. The gear wheel 9 engages teeth formed around the inner periphery of the casing 2. The rotatable member carries an extended source 11 of penetrating radiation, in this example X-rays and facing the source 11, on the other side of the aperture 3 there is a detector means 12 which will be described in greater detail hereinafter. At the source 11 a plurality of collimators 13, in this example eight, form a plurality of pencil beams of radiation, such as 14 from the sheet of radiation, normal to the axis of aperture 3 formed by the source 11. Corresponding collimators 15 provided at detector means 12 further define these pencil beams and serve to substantially exclude scattered radiation from the detector means.

The source 11 is secured to a toothed belt 16 driven by a toothed drive shaft 17 journalled in the rotatable member 1, the belt being extended between the shaft 17 and a second shaft 18, also journalled in member 1. The shaft 17 is driven by a reversible motor 19, the controls of which are interlocked with those of motor 10. A counter weight 20 is provided, secured to the other run of the belt so as to move reciprocally with the source. In operation the source 11 and collimators 13 are caused by the motor 19 to execute to and fro lateral scanning movements in the aforementioned plane normal to the axis of aperture 3. The detector means 12 and collimators 15 are coupled to the source 11 by a yoke 21 so that they execute the same lateral scanning movements. Guides 22 and 23 are provided to support the source 11 and detector means 12 respectively during the scanning. The broken line 14' shows the position of the pencil beam 14 at the other extremity of the scan.

Compensating means 24 are provided so that, for all positions of the lateral scan the absorption suffered by the radiation does not substantially vary as a result of the variation of path length across ring 7 and the contents thereof. Means 24 may be of any suitable absorbing material such as perspex, aluminium or carbon and are of a size appropriate to the material chosen.

At the end of each lateral scan motor 10 provides an orbital movement of member 1 through a predetermined angle, say two-thirds of a degree so as to repeat the lateral scan at a different angular position in the plane of examination. Such scans are repeated over a total angular range of, in this example, 180°. A photocell device 25, co-operating with a graticule not shown, is provided to indicate the progress of the orbital motion and a similar photocell device 25' and graticule, not shown, are provided indicate the progress of the lateral motion.

It is desired to provide, for successive positions of the lateral scans, signals representing the absorption suffered by a pencil beam of radiation at the centre of the spread of beams defined by collimators 13 and 15. For that purpose the signals provided for each such position for each beam such as 14 are appropriately weighted and combined to give the desired absorption value, but with the signals having the desired spatial frequency characteristics. The convolution function according to which the absorption values are weighted is the function shown in FIG. 2a. In that figure the co-ordinate $x$ measures the distance along the direction of traverse, i.e. normal to the pencil beams of radiation, with respect to an origin 0 which is placed at the centre of the spread of the pencil beams. The weighting function is plotted as the curve shown against $x$ as the function variable. The curve chosen in this example is the graph of $$\frac{\sin 2\pi f x}{x}$$

In that case sampling the absorption data weighted according to the curve ensures that all the Fourier components of absorption integrals, nominally for the pencil beam incident at origin 0, are preserved without relative emphasis or de-emphasis for frequencies up to the frequency $f$, but components of higher frequency than $f$ are not represented. If the sampling frequency used by the apparatus is $2f$ therefore, or higher, spurious patterns which could be formed as mentioned hereinbefore, are avoided.

It will be understood that absorption values are not obtained from the detectors instantaneously but are obtained by integration of output data signals during the lateral scan for a period long enough to obtain an adequate count. This period, in practice, defines the width of the pencil beams. The lateral scanning rate and integration period are therefore inter-related to provide the desired spatial sampling frequency.

It will be observed that the curve which lies symmetrically about the coordinate origin 0 passes successively through zero for values of $x$ equal to $½f$, $1/f$, $3/2f$, $2/f$, $5/2f$, $3/f$, ... to the right of the origin, and likewise to the left of the origin for similar but negative values of $x$. In doing so it exhibits a sequence of alternate positive and negative lobes in the intervals between successive values of $x$. FIG. 2(b) replicates these intervals, and the ordinates erected at the mid points of the intervals are intended respectively to represent the area under the curve of FIG. 2(a) over each interval, areas relative to negative lobes being represented negatively by being drawn in a downwards direction. Following the invention the lateral scanning is operated with a sampling frequency of $2f$. The detector means 12 correspondingly includes scintillation crystals, serving as radiation detectors, located one in each interval, preferably to accept incident radiation over the whole of the interval in each instance. Also following the invention the intensity of the light being transferred from a crystal to an amplifying photomultiplier is proportioned in accordance with the ordinates for the respective intervals taking into account its positive or negative sign. In this way the required weighting of the sampled data is achieved.

FIG. 3 shows one arrangement for detector means 12 including an array of detecting crystals and light guide means for achieving the weighted optical transfer described. The array shown in this example comprises eight crystals designated in sequence $26_{-4'}$ $26_{-3'}$ $26_{-2'}$ $26_{-1'}$ $26_{1'}$ $26_{2'}$ $26_3$ and $26_4$. These are to be supposed as lying symmetrically about the origin 0 of FIGS. 2(a) and (2b), the crystals $26_1$ and $26_{-1}$ each accepting radiation substantially over the whole of the two intervals which in these figures lie immediately on either side of the origin, $26_2$ and $26_{-2}$ being similarly related to the next adjacent intervals and so on. The parallel lines indicated typically at 14 represent the direction of the radiation incident upon the crystals. The array may, in practice, be considerably more extensive than that of the eight crystals shown though not necessarily so.

Reference numerals 27 and 28 designate two photomultiplier devices. Light from the crystals of the array is transferred to the photocathodes of these devices by fibre-optics bundles, one bundle respective to each crystal. Those bundles respective to crystals located in positive lobe intervals transfer light to the photocathode of photomultiplier device 27, while those respective to the remainder which are associated with negative lobe intervals transfer light to the photocathode of photomultiplier device 28. Thus the bundles $29_1$ and $29_{-1}$ feed to the device 27 from respective crystals $26_1$ and $26_{-1}$, but bundles $29_2$ and $29_{-2}$ feeding light from the next adjacent crystals $26_2$ and $26_{-2}$ respectively convey the light to device 28. To comply with the respective weighting of the light intensity the number of fibres in each bundle is appropriately adjusted, as indicated by the varying sizes of the bundles in the figure. The crystals are enveloped in light reflective coatings except at the regions of transfer to the fibre-optics bundles, so that light is not unnecessarily lost, and the ends of the fibres are arranged to make optical contact with the surfaces of transfer. The bundles $23_1$ and $23_{-1}$ are each arranged to accept all or almost all the light transmitted by the crystal face against which the fibres abutt.

FIG. 4 indicates a general arrangement of the apparatus for processing the signal outputs from the two photomultiplier circuits 27 and 28 to provide the desired representation of absorption in a display store from which it may be directly displayed, for example by cathode ray tube display or again by computer print-out.

The initial step in the processing is to subtract the signal derived from the photomultiplier 28 from that derived from the photomultiplier 27 to produce a resultant signal which represents the original absorption data after band limitation to half the sampling frequency by convolution, as explained hereinbefore, with the data acquisition weighting function represented by the curve of FIG. 2(a). The subtraction is performed by a differencing circuit 30 the output of which is applied to an integrator circuit 31. The function of this circuit is as mentioned hereinbefore to integrate the output signal from the circuit 30 for a period which substantially equals the data sampling interval of the apparatus. For this purpose it accepts signals from photocell device 25' marking predetermined positions in the lateral scan. The integrated signal from the circuit 31 is transferred to an analogue-to-digital converter circuit shown at 32, and the converted signal is then transferred to the logarithmic converter circuit 33. In the course of one complete lateral scan, of the radiation source and detector means, a correspondingly complete set of logarithmically converted absorption samples is generated. Such a set is termed a parallel set of absorption data, since it represents transmission information related to one particular direction of transmission, namely that of the angular disposition of the scanner at the time of acquisition. As the scanner takes up further angular dispositions in sequence corresponding parallel sets of data are generated. All sets as they are produced are transferred to a store 34 where they are drawn upon for convolution processing by a convolution unit 35 to transform the acquired data into data, suitable for display, showing the distribution of absorption over the cross section examined. The data in the form derived by the convolution processing in unit 35 is stored ready for display, or other utilisation, in a display matrix store 37, but in the interests of greater accuracy of representation in display it is subjected to intermediate processing in an interpolator unit 36. This is for the reason that the data as it is processed by unit 35 does not in general relate strictly to the display pattern points assumed in regard to the display store 37, but rather to nearby points of the display pattern. Since these points are known, interpolation between pairs straddling display points can yield more accurate data for these latter points, and this interpolation is performed by unit 36.

Procedures and equipment utilised as indicated by FIG. 4 in regard to convolution of sampled data for the purposes of display are set out in more detail in U.S. application Ser. No. 462104. More detailed information is also set out in that application in relation to the integration and pre-convolution processing of sampled data, and to post-convolution interpolation immediately prior to display storage.

It will be realised that the apparatus as described in relation to FIG. 3 may be operated with one photomultiplier only, to which the optical outputs of all crystals of the array are transferred, if a suitable shutter is placed directly in front of the crystals and oscillated so that alternately only positive lobe crystals are exposed to the transmitted radiation, and then only negative lobe crystals. When only negative lobe crystals are exposed the output of the photomultiplier is inverted by a suitable inverting circuit. If the oscillation rate of the shutter is sufficiently high the effect of the differencing performed by circuit 30 of FIG. 4 is accomplished in the absence of the circuit by the integrator 31.

It will be understood that the weighting effected by the optical transfers from the scintillation crystals to the photomultipliers, or photomultiplier, may alternatively be accomplished by appropriate adjustment of the aperture width of the crystals.

In an alternative embodiment the weighting function is applied entirely in the processing circuits. It will be understood that, in the course of a lateral scan each of the detectors shown in FIG. 3 takes up substantially all of the positions shown. Consequently data from a single detector, with appropriate time sequencing and weighting, gives all the data provided by the arrangement of FIG. 3.

The apparatus used is similar to that of FIG. 1 except that the source and detector means are replaced by a point source and single detector respectively. These, and the associated collimators, may be as described in the said British Patent.

A modified block diagrammatic circuit for this embodiment is shown in FIG. 5. The single photomultiplier 38 supplies identical output signals to amplifiers $39_1$ to $39_4$. It will be appreciated that in FIG. 3, pairs of detectors such as $26_1$ and $26_{-1}$ convey substantially identical information to their respective photomultipliers, when they cover the same sampling position. Consequently in the arrangement of FIG. 5 only four channels are needed although the outputs of each are used twice. The amplifiers 39 have gains maintained in a fixed relationship so that the signals on each channel are respectively weighted according to the function of FIG. 2(a). The weighted signals in each channel are integrated over the sampling period by integrators $40_1$ to $40_4$ in response to signals from photodetector $25'$ and converted into digital form in converters $41_1$ to $41_4$ before being supplied to computer 42, which is a suitably programmed digital computer.

It will be understood that, although the four channels supply all the data which would have been supplied via photomultipliers 27 and 28 in FIG. 4, they do so in an incorrect time relationship. Computer 42 therefore stores the signals in appropriate storage location, one positive and one negative from each channel until all signals appropriate to one set are received and then combines them to form the weighted sum as described hereinbefore. For this purpose computer 42 accepts input signals from photodetector unit $25'$, indicating the progress of the lateral scan. As each weighted sum signal is assembled it is applied to store 34 via logger 33 as before.

In practice the computer 42 can, if suitably programmed, carry out the functions of other units such as store 34, processor 35 and interpolator 36. Similarly the units shown in FIG. 4 can, if desired, be replaced with a suitably programmed digital computer.

It will be understood that other arrangements may be devised to provide a weighted sum of absorption data signals according to the principle of the invention.

What we claim is:

1. An apparatus for examining a body by means of penetrating radiation such as X- or $\gamma$-radiation including source means arranged to irradiate a substantially planar region of the body, detector means responsive to said radiation and disposed to receive the radiation after passage through the body, means for scanning the source and detector means with respect to the body to irradiate the body along a plurality of sets of substantially parallel beam paths in the plane of said region, the paths of each set being spaced laterally from one another and means for constructing output signals, each from values of the intensity of radiation received along different paths of a set, weighted by respective factors, the weighting factors being chosen according to a predetermined function so that spatial frequency components of the output signals, resulting from variations in the absorption of the radiation in the direction of the lateral spacing, are limited to a predetermined spatial frequency band, and further including means arranged to provide signals, which are logarithms of said output signals, for processing to construct a representation of the distribution of absorption with position in the said planar region.

2. An apparatus according to claim 1 wherein the said function approximates to $$\frac{\sin 2\pi fx}{x}$$

where $x$ represents the position in a direction perpendicular to the parallel beam paths from a predetermined origin and $f$ is the frequency limit of the said frequency band.

3. An apparatus according to claim 1 wherein the said detector means includes a plurality of detectors and the said means for constructing includes means for weighting the outputs of those detectors according to the said function.

4. An apparatus according to claim 3 wherein the said detectors are scintillator crystals and the weighting means comprises respective light guides arranged to transmit light emitted by the crystals to at least one photomultiplier and to modify the intensity of the light according to the said function.

5. An apparatus according to claim 4 having two photomultipliers and means for combining the outputs of those photomultipliers.

6. An apparatus according to claim 4 having one photomultiplier and including shutter means arranged to interrupt the light output of said crystals in predetermined sequence.

7. An apparatus according to claim 6 wherein the said shutter means is arranged to interrupt the radiation incident on said crystals.

8. An apparatus according to claim 1 wherein said means for constructing includes means for weighting signals derived from the detector means according to the said function and means for combining the weighted signals in a sequence related to the position in the said planar region, of the beam paths to which they are related.

9. A medical radiographic apparatus for a diagnostic examination of a substantially planar section through the body of a patient, comprising: means disposed outside the body for generating penetrating radiation which propogates substantially along the plane of the section, traverses the body and emerges therefrom after suffering absorption determined at least in part by its path through the body; detecting means responsive to the radiation and disposed to determine the intensity of radiation which has traversed the body; a scanning frame on which the generating means and detecting means are mounted to provide relative motions between the generating means and detecting means on the one hand and the patient on the other hand, said motions including an orbital motion of the generating means and detecting means substantially in the plane about an axis perpendicular to the plane and a lateral motion of the generating means and detecting means substantially in the plane, so that the detecting means determines the intensity of radiation which has traversed the body along a plurality of sets of substantially parallel beam paths lying in the said plane; means for combining the determinations of intensity to provide a plurality of output signals the amplitude of each of which is related to values of the intensity of radiation, received by the detecting means after traversing the body along respective parallel paths of a set, weighted by respective factors, the weighting factors being chosen according to a predetermined function so that spatial frequency components of the output signals, resulting from changes in the determined intensities in the direction of the lateral motion, are limited to a predetermined range of spatial frequencies; means arranged to provide further signals which are logarithms of the said output signals; and means for combining the said further signals and for constructing an image of the said planar section, said image comprising a matrix of image elements representing absorption coefficients to the radiation of corresponding elements not ionally defined in the said planar section.

* * * * *